(12) United States Patent
Yoshioka et al.

(10) Patent No.: US 9,633,167 B2
(45) Date of Patent: Apr. 25, 2017

(54) INFORMATION PROCESSING APPARATUS, METHOD AND PROGRAM FOR PERFORMING A ZOOMING OPERATION

(75) Inventors: Shigeatsu Yoshioka, Kanagawa (JP); Masao Kondo, Tokyo (JP); Yutaka Hasegawa, Kanagawa (JP)

(73) Assignee: Sony Corporation, Tokyo (JP)

(*) Notice: Subject to any disclaimer, the term of this patent is extended or adjusted under 35 U.S.C. 154(b) by 466 days.

(21) Appl. No.: 13/084,995

(22) Filed: Apr. 12, 2011

(65) Prior Publication Data

US 2011/0254866 A1  Oct. 20, 2011

(30) Foreign Application Priority Data

Apr. 16, 2010  (JP) ................ 2010-095531

(51) Int. Cl.
  *G09G 5/00*   (2006.01)
  *G06F 19/00*  (2011.01)
(52) U.S. Cl.
  CPC ........ *G06F 19/321* (2013.01); *G06F 19/3406* (2013.01); *G06F 2203/04806* (2013.01)
(58) Field of Classification Search
  CPC ............ G06F 2203/04806; G06T 3/40; G09G 2340/045
  USPC .................................. 345/660–671
  See application file for complete search history.

(56) References Cited

U.S. PATENT DOCUMENTS

| 5,526,018 | A  | * | 6/1996  | Fisher ........................... 345/668 |
| 6,281,874 | B1 | * | 8/2001  | Sivan et al. .................. 345/660 |
| 2005/0094033 | A1 | * | 5/2005  | Schoner et al. .............. 348/558 |
| 2005/0270311 | A1 | * | 12/2005 | Rasmussen et al. .......... 345/677 |
| 2008/0204476 | A1 | * | 8/2008  | Montague ..................... 345/661 |
| 2010/0299641 | A1 | * | 11/2010 | Cundill ......................... 715/863 |
| 2012/0076471 | A1 | * | 3/2012  | Ciudad ............... H04N 1/00286 386/278 |

FOREIGN PATENT DOCUMENTS

| JP | 03-226796   | 10/1991 |
| JP | 04-222063   | 8/1992  |
| JP | 08-106542   | 4/1996  |
| JP | 2001-061165 | 3/2001  |
| JP | 2008-197736 | 8/2008  |
| JP | 2009-031250 | 2/2009  |

OTHER PUBLICATIONS

Japanese Office Action issued Dec. 10, 2013 for corresponding Japanese Appln. No. 2010-095531.
Japanese Office Action issued Apr. 22, 2014 for corresponding Japanese Appln. No. 2010-095531.
Japanese Office Action issued Sep. 24, 2014 for corresponding Japanese Appln. No. 2010-095531.
Chinese Office Action issued Oct. 10, 2014 for corresponding Chinese Appln. No. 201110089231.0.

* cited by examiner

*Primary Examiner* — Kyle Zhai
(74) *Attorney, Agent, or Firm* — K&L Gates LLP

(57) ABSTRACT

An information processing apparatus, method, and program are provided that control display of an image. The information processing apparatus, method, and program designate a first point and a second point on an image, determine a zoom direction based on a position of the first point relative to a position of the second point, and zoom the image in the zoom direction.

15 Claims, 9 Drawing Sheets

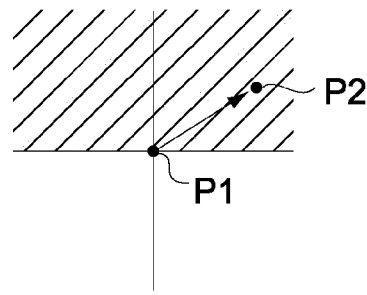
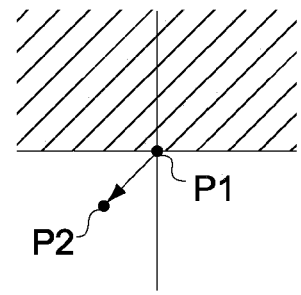
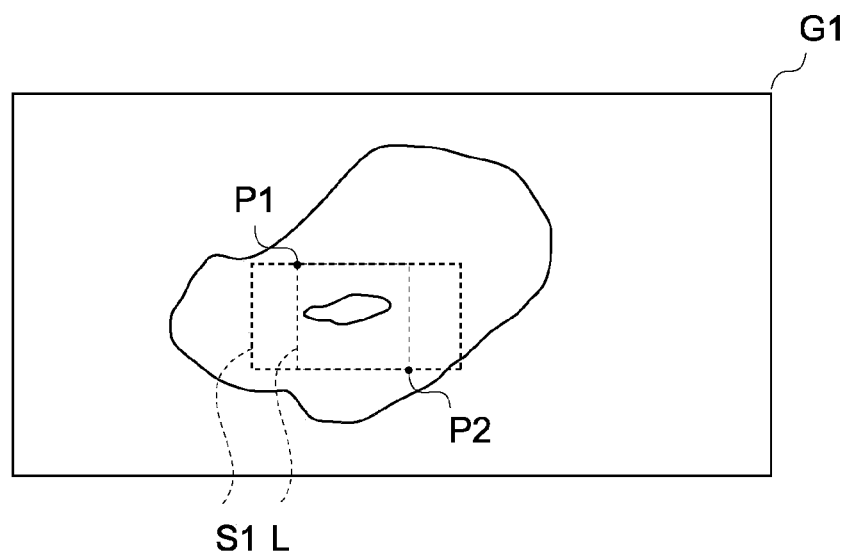
FIG.7

INFORMATION PROCESSING APPARATUS, METHOD AND PROGRAM FOR PERFORMING A ZOOMING OPERATION

CROSS-REFERENCE TO RELATED APPLICATIONS

The present application claims priority to Japanese Patent Application JP 2010-095531, filed in the Japanese Patent Office on Apr. 16, 2010, the entire contents of which is being incorporated herein by reference.

BACKGROUND

The present disclosure relates to an information processing apparatus, a method, and a program therefore that control display of an image obtained by a microscope in the field of medicine, pathology, biology, materials science, or the like.

In the field of medicine, pathology, or the like, there has been proposed a system that digitizes an image of a cell, a tissue, an organ, or the like of a living body, which is obtained by an optical microscope, to examine the tissue or the like by a doctor or a pathologist or to diagnose a patient based on the digitized image.

For example, Japanese Patent Application Laid-open No. 2009-37250 (hereinafter, referred to as Patent Document 1) discloses a method in which an image optically obtained by a microscope is digitized by a video camera with a CCD (charge coupled device), a digital signal is input to a control computer system, and an image is visualized on a monitor. A pathologist performs examination or the like while watching the image displayed on the monitor (see, for example, paragraphs 0027 and 0028 and FIG. 5 of Patent Document 1).

SUMMARY

Such a system allows various operations to be made on an image displayed on a monitor in response to an operation input made by a user using an input means such as a mouse. Here, the operations performed on an image are, for example, movement, rotation, zoom-in, and zoom-out of a display range of the image. By those operations, the user can observe the image as if the user actually operated a microscope.

In the system as described above, in a case where a user wants to observe an image partially enlarged, generally, the user moves an observation target area to the center of a screen and then designates a zoom magnification, for example. However, to move an image, it is necessary to operate an input means such as a mouse and a keyboard by an amount corresponding to a movement distance of the image. For example, it is necessary to make an operation of moving a mouse by an amount corresponding to a distance by which an image is intended to be moved, an operation of pressing a key of a keyboard the number of times corresponding a distance by which an image is intended to be moved, and the like.

In this regard, there is conceived a method of designating a point on an image and a value of a zoom magnification to enlarge the image at the designated zoom magnification, with the designated point as the center. However, in this case, the operation of designating the enlargement center point on the image and the operation of designating the value of a zoom magnification, that is, at least two discontinuous designation operations are needed. In this way, when the discontinuous operations are necessary for one operation on an image, the operation efficiency is adversely affected to a large extent in such a situation that a large number of images have to be speedily processed particularly in the field of medicine or the like, and there is a demand for improvement thereof.

In view of the circumstances as described above, it is desirable to provide an information processing apparatus, method, and a program that are capable of changing the zoom magnification of a display image speedily.

In an embodiment, an information processing apparatus includes a processor and a memory device. The memory device stores instructions which when executed by the processor, cause the processor to designate a first point and a second point on an image, determine a zoom direction based on a position of the first point relative to a position of the second point, and zoom the image in the zoom direction.

In the information processing apparatus of an embodiment, the instructions further cause the processor to determine a zoom magnification based on the position of the first point relative to the second point, wherein the image is zoomed in the zoom direction at the zoom magnification.

In the information processing apparatus of an embodiment, the instructions further cause the processor to set a first area that is defined based on the first point and the second point, wherein the zoom magnification is determined based on the first area.

In the information processing apparatus of an embodiment, the first area is a rectangular area having the first point and the second point at two opposite corners.

In the information processing apparatus of an embodiment, the instructions further cause the processor to set a candidate area in the image based on the zoom direction and the first area, wherein the zoom magnification is determined based on the candidate area.

In the information processing apparatus of an embodiment, the zoom magnification is determined based on a comparison of a size of the candidate area and a size of the image.

In the information processing apparatus of an embodiment, when the zoom direction is determined to be zoom-in, the candidate area is set as a minimum area having a same aspect ratio as the image and including the first area.

In the information processing apparatus of an embodiment, when the zoom direction is determined to be zoom-out, the candidate area is set as a maximum area having a same aspect ratio as the image and included in the first area.

In the information processing apparatus of an embodiment, the instructions further cause the processor to generate a zoomed image by zooming the image, wherein the candidate area is at a center of the zoomed image.

In the information processing apparatus of an embodiment, the instructions further cause the processor to generate a zoomed image by zooming the image, wherein a center of the zoomed image is between the first point and the second point.

The information processing apparatus of an embodiment further includes a storage unit configured to store image data having different resolutions in hierarchical layers. The instructions further causing the processor to determine a zoom magnification based on the position of the first point relative to the second point, wherein the image is zoomed by reading out image data at a hierarchical layer having a resolution corresponding to the zoom magnification.

The information processing apparatus of an embodiment further includes an input device and a display. The instructions further causing the processor to display the image on the display, designate the first point and the second point according to an input received by the input device, and display a zoomed image according to the input received by the input device.

In the information processing apparatus of an embodiment, the image is of a pathological tissue sample captured by a microscope.

In an embodiment, an information processing method includes designating a first point and a second point on an image, determining a zoom direction based on a position of the first point relative to a position of the second point, and zooming the image in the zoom direction.

In an embodiment, a non-transitory computer readable storage medium stores a computer program for causing an information processing apparatus to designate a first point and a second point on an image, determine a zoom direction based on a position of the first point relative to a position of the second point, and zoom the image in the zoom direction.

Additional features and advantages are described herein, and will be apparent from the following Detailed Description and the figures.

BRIEF DESCRIPTION OF THE DRAWINGS

FIG. 6 are Each schematic diagrams for explaining a judgment made by the judgment unit.

FIG. 7 is a schematic diagram showing a display image in which a candidate area is set.

DETAILED DESCRIPTION

The present application is described in further detail below with reference to the drawings according to an embodiment.

Structure of Information Processing Apparatus

Figure 1:
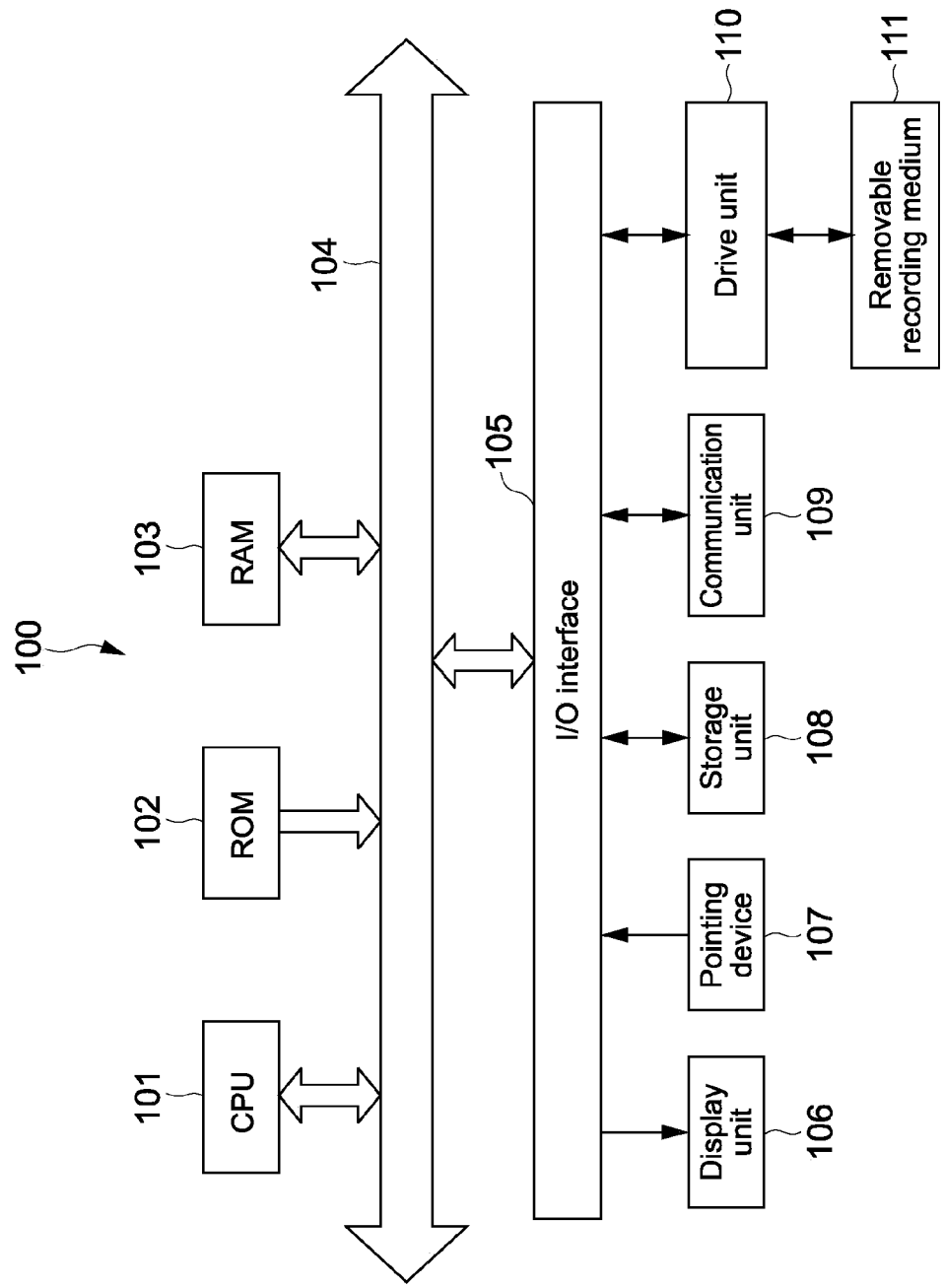
FIG. 1 is a block diagram showing the structure of a computer system including an information processing apparatus.

FIG. 1 is a block diagram showing the structure of a computer system including an information processing apparatus according to an embodiment. As the information processing apparatus, a PC (personal computer) 100 is used, for example.

The PC 100 includes a CPU (central processing unit) 101, a ROM (read only memory) 102, a RAM (random access memory) 103, an input and output interface (hereinafter, abbreviated as I/O interface) 105, and a bus 104 that connects those components with one another.

To the I/O interface 105, a display unit 106, a pointing device 107, a storage unit 108, a communication unit 109, a drive unit 110, and the like are connected.

The display unit 106 is a display device that uses liquid crystal, EL (electro-luminescence), a CRT (cathode ray tube), or the like.

The pointing device 107 is a device capable of indicating a point on a display screen of the display unit 106, such as a mouse, a trackball, and a touch pad. The pointing device 107 is provided with buttons that allow operations such as a click and a drag.

The storage unit 108 is a non-volatile memory such as an HDD (hard disk drive), a flash memory, and another solid-state memory.

The drive unit 110 is a device capable of driving a removable recording medium 111 such as an optical recording medium, a floppy (registered trademark) disk, a magnetic recording tape, and a flash memory. In contrast, the storage unit 108 is often used as a device that is previously included in the PC 100 and mainly drives a recording medium that is not removable.

The communication unit 109 is a modem, a router, or another communication device that is connectable to a LAN (local area network), a WAN (wide area network), or the like and is used for communicating with another device. The communication unit 109 may perform one of a wired communication or a wireless communication. The communication unit 109 is used separately from the PC 100 in many cases.

Pyramid Structure of Image Data and Access to Image Data

Next, description will be given on image data that is to be processed by an information processing apparatus (PC 100) of this embodiment.

Figure 2:
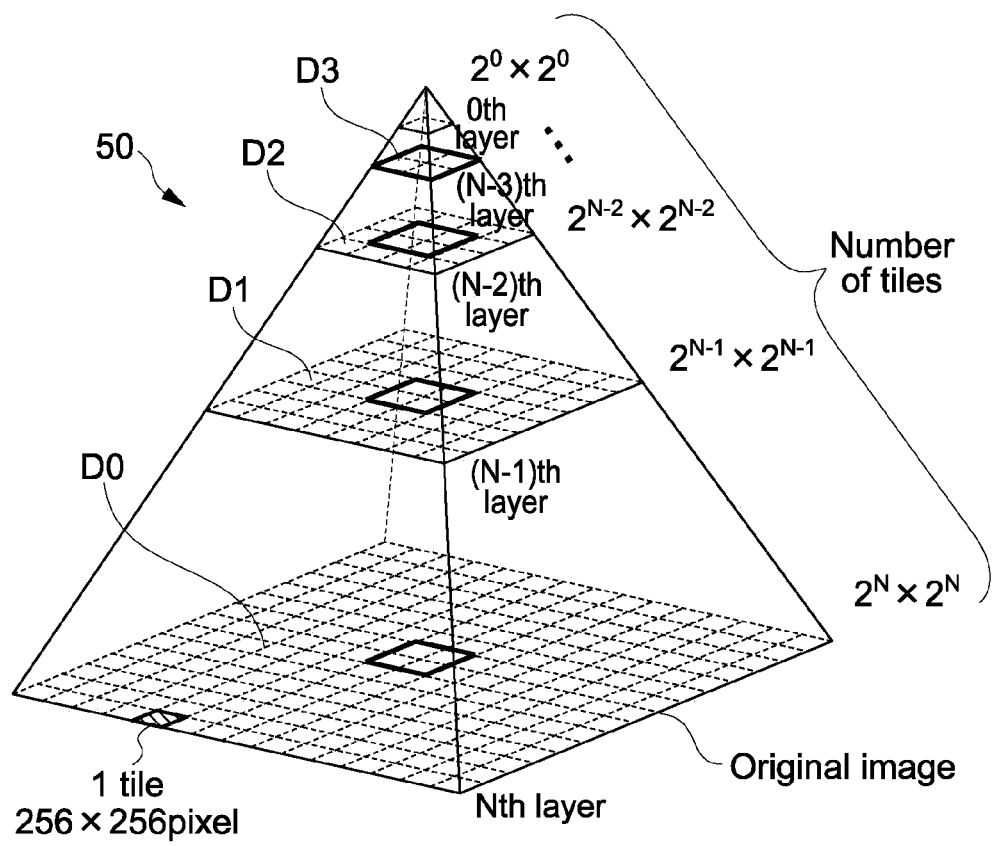
FIG. 2 is a conceptual diagram showing the pyramid structure of image data.

FIG. 2 is a diagram showing the pyramid structure of image data.

As shown in FIG. 2, the image data to be processed is in the pyramid structure of image data obtained by capturing an image of an observation target with a high-resolution imaging means, for example. The pyramid structure of image data is formed by generating pieces of image data having different resolutions that are lowered in a stepwise manner from the resolution of the image data originally captured, and setting those pieces of image data in a hierarchical manner. The image data in each layer is divided into areas, each of which is referred to as a "tile" and has a predetermined resolution. Assuming that the layers of the pyramid structure are referred to as an Nth layer, an (N−1)th layer, an (N−2)th layer, . . . , and a 0th layer from the bottom of the pyramid, the numbers of tiles in the layers are $2^N \times 2^N$, $2^{N-1} \times 2^{N-1}$, $2^{N-2} \times 2^{N-2}$, . . . , and 1, respectively. It should be noted that the resolution of one tile is, for example, 256×256 (pixels) or 256×512 (pixels).

Upon receiving a designation on an arbitrary resolution and a display range of an image from a user, the information processing apparatus (PC 100) reads image data corresponding to the designation from the image pyramid structure in unit of tile, and expands the image data in a display buffer to display an image on the display unit 106.

Further, in a case where an instruction is given by the user to move a display range of the image displayed on the display unit 106 (hereinafter, the image is referred to as display image), the information processing apparatus (PC 100) reads, in response to the instruction, image data of a movement destination from the pieces of image data having the same resolution in unit of tile, and updates information in the display buffer to display the image of the instructed movement destination on the display unit 106. It should be noted that the "display range of image" refers to an area of image data displayed in reality on a physical screen, in the entire image data.

In addition, in a case where an instruction is given by the user to change a zoom magnification for display (zoom-in/zoom-out) by operations described later, the information processing apparatus (PC 100) reads, out of pieces of image data having a resolution corresponding to a designated zoom magnification, necessary image data in unit of tile, and updates the information of the display buffer to change the zoom magnification of the display image. It should be noted in a case where the size of an image display area on the physical screen is fixed, the display range of an image is reduced when the zoom magnification is increased (at zoom-in), and conversely, the display range of an image is enlarged when the zoom magnification is reduced (at zoom-out). In this way, it is possible to shorten a time necessary to access image data as a whole by reading necessary image data in unit of tile from the pyramid structure of image data.

Functional Structure of Information Processing Apparatus

Figure 3:
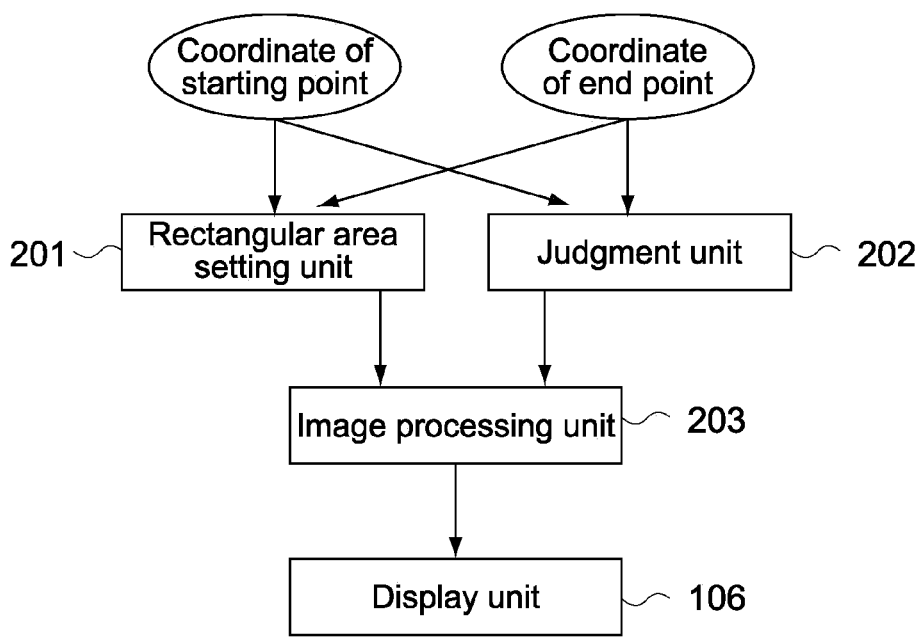
FIG. 3 is a block diagram showing the functional structure of the information processing apparatus.

FIG. 3 is a diagram showing the functional structure of the information processing apparatus (PC 100) according to this embodiment.

As shown in FIG. 3, the information processing apparatus (PC 100) of this embodiment includes a rectangular area setting unit 201, a judgment unit 202, and an image processing unit 203. Those functional units are provided as a program for causing the typical computer described above to function. The program is stored in, for example, a storage means such as the storage unit 108. In order to display image data on the display unit 106, the CPU 101 loads the program into the RAM 103 as a main memory from the storage unit 108, to interpret and execute the program. The schematic structures of the functional units are as follows.

As shown in FIG. 3, the rectangular area setting unit 201 sets a "rectangular area" based on the coordinates of the positions of a starting point and an end point that are designated with use of the pointing device 107, and supplies the information of the "rectangular area" to the image processing unit 203. The judgment unit 202 judges, based on the direction to the end point from the starting point, whether an operation made with use of the pointing device 107 is an operation of increasing the zoom magnification of a display image (zoom-in) or reducing the zoom magnification thereof (zoom-out). Then, the judgment unit 202 supplies a judgment result to the image processing unit 203.

Based on the information of the rectangular area and the judgment result supplied from the judgment unit 202, the image processing unit 203 sets a "candidate area", compares the size of the candidate area with that of the display image, and determines a zoom magnification. Then, the image processing unit 203 generates an image at the zoom magnification with the candidate area as the center and displays the image on the display unit 106.

Operation of Information Processing Apparatus

The operation of the information processing apparatus (PC 100) will be described.

Figure 4:
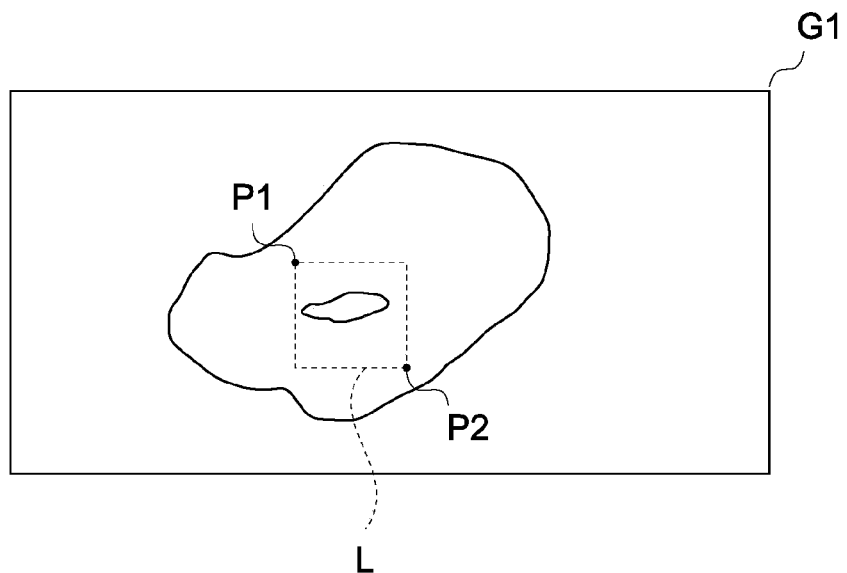
FIG. 4 is a schematic diagram showing a display image in which a rectangular area is set.

FIG. 4 shows a display image G1 displayed on the display unit 106. It should be noted that the display image G1 is one of the images described when the image pyramid has been described above, for example, an image of the (N−3)th layer. Here, as an example of the display image G1, an image of a pathological tissue sample is shown.

As shown in FIG. 4, a starting point and an end point that are designated with the pointing device 107 being operated by the user are represented as a starting point P1 and an end point P2, respectively. The starting point P1 and the end point P2 are set, for example, as a starting point and an end point obtained when the pointing device 107 is dragged.

When the starting point P1 and the end point P2 are designated, the rectangular area setting unit 201 sets a "rectangular area" L based on the coordinates of the positions of the starting point P1 and the end point P2. The rectangular area L is a rectangular area having the line connecting the starting point P1 and the end point P2 as a diagonal line. It should be noted that the rectangular area L is internally processed in the information processing apparatus in reality, and is not displayed on the display unit 106.

Further, when the starting point P1 and the end point P2 are designated, the judgment unit 202 judges whether the operation made by the user is an operation of increasing the zoom magnification (hereinafter, referred to as zoom-in operation) or reducing the zoom magnification (hereinafter, referred to as zoom-out operation), based on the direction to the end point P2 from the starting point P1. FIGS. 5 and 6 are schematic diagram for explaining the judgment made by the judgment unit 202.

Figure 5A:
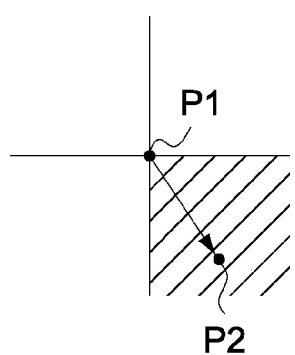
FIG. 5 are each schematic diagrams for explaining a judgment made by a judgment unit.
Figure 5B:
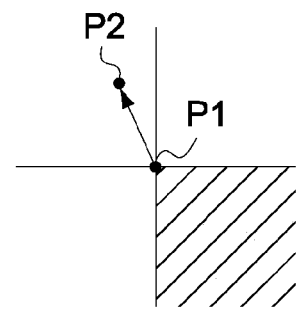

For example, as shown in FIG. 5A, if the end point P2 exists in the lower right direction indicated by an oblique line with the position of the starting point P1 as the center, the judgment unit 202 judges that a zoom-in operation has been made. As shown in FIG. 5B, if the end point P2 exists in any direction other than the lower right direction, the judgment unit 202 judges that a zoom-out operation has been made.

In addition, as shown in FIG. 6A, if the end point P2 exists in the upper direction with the position of the starting point P1 as the center, the judgment unit 202 may judge that a zoom-in operation has been made, and as shown in FIG. 6B, if the end point P2 exists in the lower direction, the judgment unit 202 may judge that a zoom-out operation has been made. In this way, the direction of a zoom-in operation or a zoom-out operation judged by the judgment unit 202 is arbitrarily set, that is, a direction in which an operation is easily made by a user may be set. As described above, the judgment unit 202 judges a zoom-in operation or a zoom-out operation based on the position of the end point P2 with respect to the starting point P1, with the result that the user can designate zoom-in or zoom-out of a display image based on only the direction in which the pointing device 107 is moved, which is convenient.

It should be noted that the judgment unit 202 may judge by other methods whether a zoom-in operation has been made or a zoom-out operation has been made. For example, when the starting point P1 and the end point P2 are designated and a drag is performed, if a button provided to the pointing device 107 is being pressed, the judgment unit 202 may judge that the operation is a zoom-out operation, and if the button is not being pressed, the judgment unit 202 may judge that the operation is a zoom-in operation.

Hereinafter, a case where the judgment unit 202 judges that the user has made a zoom-in operation and a case where the judgment unit 202 judges that the user has made a zoom-out operation will be described separately from each other. First, the case where the judgment unit 202 judges that a zoom-in operation has been made will be described.

Figure 8:
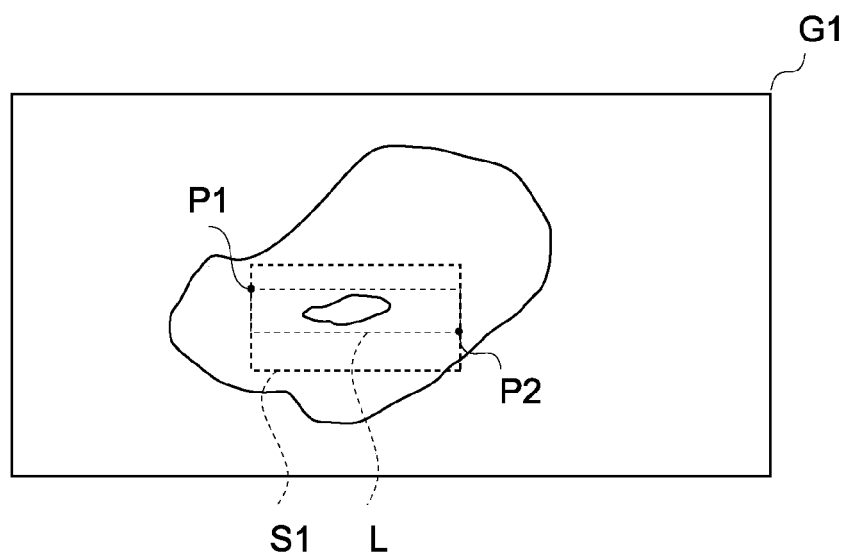
FIG. 8 is a schematic diagram showing a display image in which a candidate area is set.

Based on the judgment of a zoom-in operation, the image processing unit 203 sets a candidate area. FIG. 7 is a diagram for explaining the setting of a candidate area S1. As shown in FIG. 7, the image processing unit 203 sets a candidate area S1 including a rectangular area L. Here, the candidate area S1 is a minimum area that is similar to the display image G1 and includes the rectangular area L. Therefore, the candidate area S1 comes into contact with at least one of short sides and long sides of the rectangular area L. FIG. 8 shows a candidate area S1 in which the shape of the rectangular area L is different from that of FIG. 7.

Figure 9:
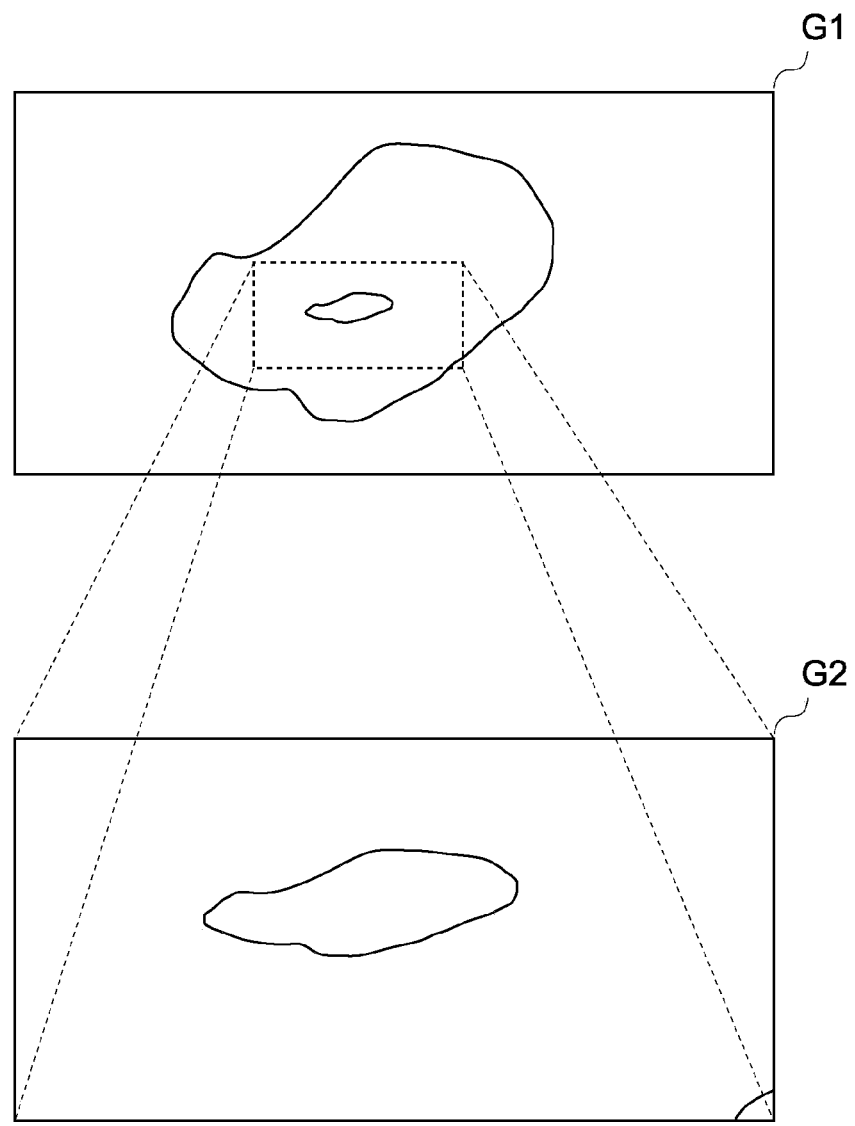
FIG. 9 is a schematic diagram showing a zoomed-in display image.

Subsequently, the image processing unit 203 selects, from the image pyramid, image data having a zoom magnification at which each side of an image included in the candidate area S1 of the display image G1 (hereinafter, partial image) coincides with that of the display image G1. Then, a display range that coincides with the candidate area S1 is selected and displayed on the display unit 106. Accordingly, the zoom magnification is increased from that the display image G1 (zoom-in). FIG. 9 is a diagram showing a display image G2 obtained by zooming in the display image G1.

It should be noted that the image processing unit 203 may display a frame line indicating the candidate area S1 so as to overlap the display image G1 before zooming in the display image G1, and zoom in the display image G1 upon reception of a confirmation instruction made by the user. Further, the image processing unit 203 may zoom in the display image G1 immediately after the candidate area S1 is set, without displaying the frame line indicating the candidate area S1.

Since the candidate area S1 is set as described above, the rectangular area L designated by the user based on the starting point P1 and the end point P2 is fully included in the display image G2. Therefore, the user merely has to intuitively designate a part to be observed in the display image G1 by using the pointing device 107 so as to observe an image of the part at high magnification. In other words, the user does not need to designate a zoom magnification or move a part to be observed in the display image G1 to around the center of the display image G1, with the result that the zoom magnification of the display image G1 can be increased speedily by continuous operations.

Next, description will be given on the case where the judgment unit 202 judges that a zoom-out operation has been made by a user.

Figure 10:
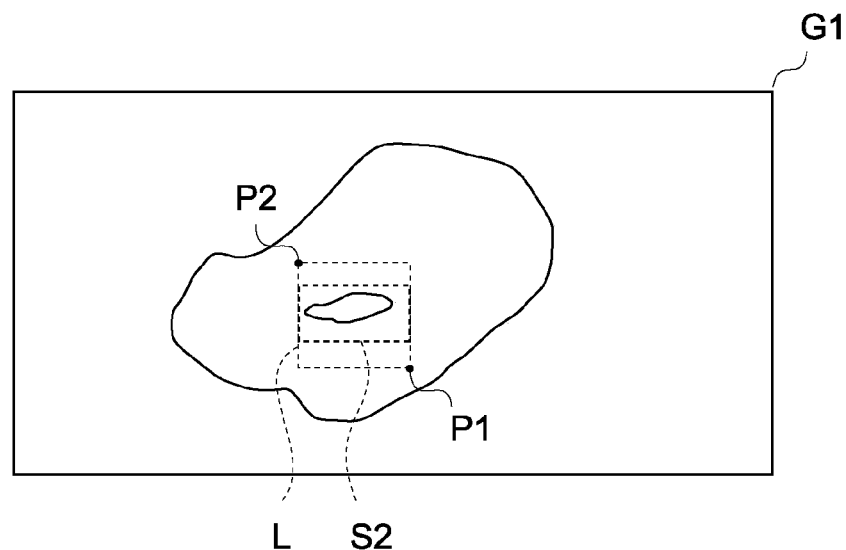
FIG. 10 is a schematic diagram showing a display image in which a candidate area is set.
Figure 11:
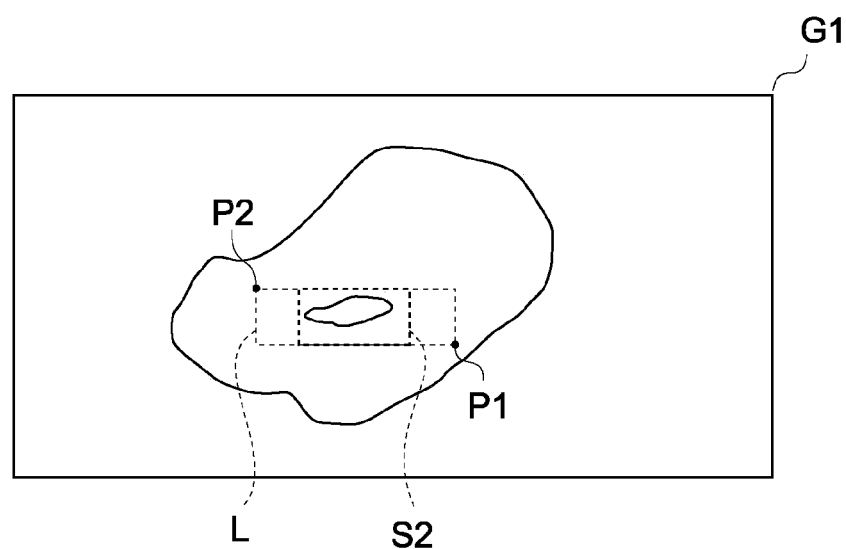
FIG. 11 is a schematic diagram showing a display image in which a candidate area is set.

Based on the judgment of a zoom-out operation, the image processing unit 203 sets a candidate area. FIG. 10 is a diagram for explaining the setting of a candidate area S2. As shown in FIG. 10, the image processing unit 203 sets a candidate area S2 included in the rectangular area L. Here, the candidate area S2 is a maximum area that is similar to the display image G1 and is included in the rectangular area L. Therefore, the candidate area S2 comes into contact with at least one of short sides and long sides of the rectangular area L. FIG. 11 shows a candidate area S2 in which the shape of the rectangular area L is different from that of FIG. 10.

Figure 12:
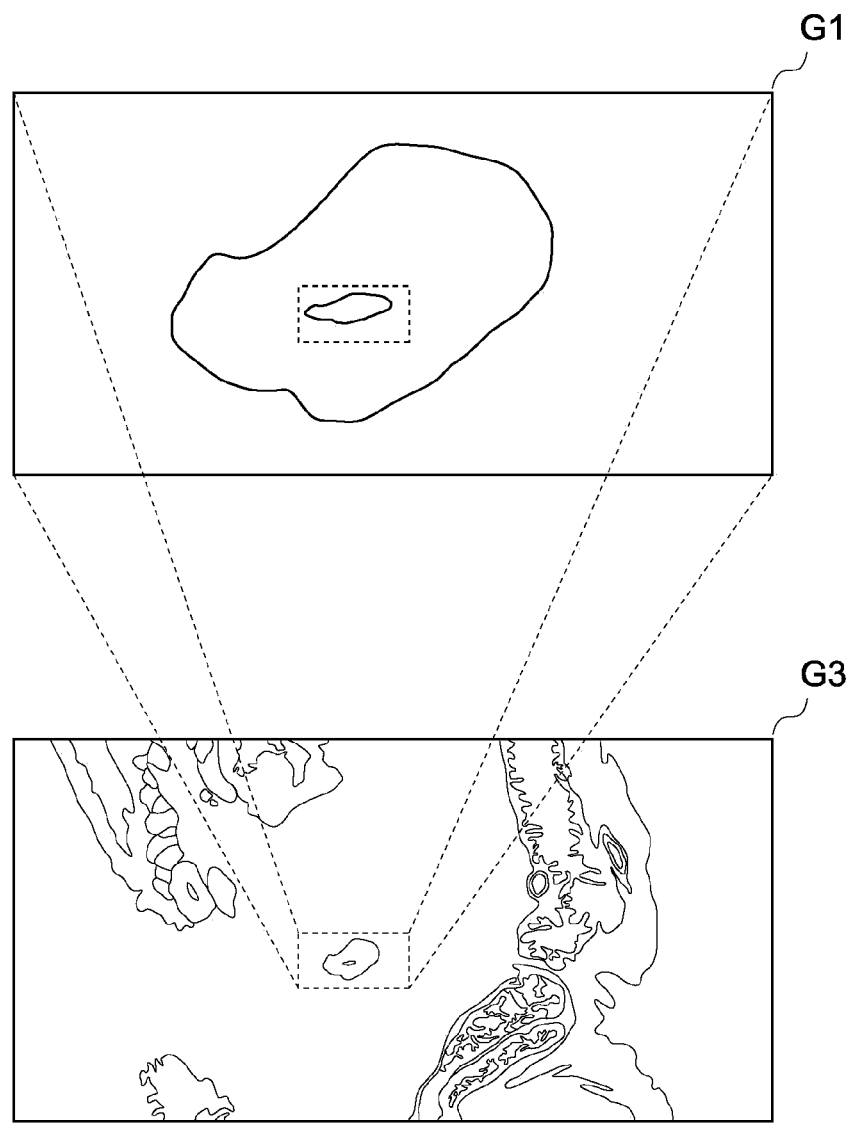
FIG. 12 is a schematic diagram showing a zoomed-out display image.

Subsequently, the image processing unit 203 selects, from the image pyramid, image data having a zoom magnification at which each side of the display image G1 coincides with that of an image included in the candidate area S2 (hereinafter, partial image). Then, a display range is selected such that the candidate area S2 is located at the center of the display range, and is displayed on the display unit 106. Accordingly, the zoom magnification is reduced from that of the display image G1 (zoom-out). FIG. 12 is a diagram showing a display image G3 obtained by zooming out the display image G1.

It should be noted that the image processing unit 203 may display a frame line indicating the candidate area S2 so as to overlap the display image G1 before zooming out the display image G1, and zoom out the display image G1 upon reception of a confirmation instruction made by the user. Further, the image processing unit 203 may zoom out the display image G1 immediately after the candidate area S2 is set, without displaying the frame line indicating the candidate area S2.

Since the candidate area S2 is set as described above, the display image G3 is displayed with the rectangular area L designated by the user based on the starting point P1 and the end point P2, as the center. Therefore, the user merely has to intuitively designate a part of the display image G1, the surroundings of which are to be observed, by using the pointing device 107 so as to observe an image with the part located at the center at low magnification. In other words, the user does not need to designate a zoom magnification or move a part to be observed in the display image G1 to the vicinity of the center of the display image G1, with the result that the display image G1 can be reduced in size speedily by continuous operations.

As described above, the information processing apparatus (PC 100) sets a rectangular area L based on a starting point P1 and an end point P2 that are designated by a user using the pointing device 107, and increases or reduces the zoom magnification of a display image G1 based on the rectangular area. Accordingly, the information processing apparatus (PC 100) allows the user to intuitively select a part of a display image, on which attention is to be focused, without separately designating the position on the display image G1, which becomes the center of the zoom magnification change, or the zoom magnification, and to speedily change the zoom magnification of a display image. As a result, the information processing apparatus (PC 100) is particularly suitable for a case where a large number of images need to be processed speedily, such as when images of pathological tissue samples are observed.

In the embodiment described above, the information processing apparatus uses a rectangular area set by a user in both the cases where the display image is zoomed in and zoomed out, but the present invention is not limited thereto. For example, it may be possible to use a rectangular area in the case where the display image is zoomed in, whereas it may be possible to use no rectangular area in the case where the display image is zoomed out. In this case, when an instruction to perform zoom-out is input, the information processing apparatus can perform zoom-out with an image being currently displayed as the center.

It should be understood that various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An information processing apparatus comprising:
a processor; and
a memory device storing instructions which when executed by the processor, causes the processor to:
(a) designate a first point and a second point on an image;
(b) determine a zoom direction based on a position of the first point relative to a position of the second point;
(c) set a first area that is defined based on the first point and the second point, and the first area is a rectangular area having the first point and the second point at two opposite corners;
(d) set a candidate area in the image based on the zoom direction and the first area, wherein the candidate area is different from the first area, the candidate area includes at least a part of the first area, and the candidate area comes into contact with at least one of short sides and long sides of the rectangular area;
(e) determine a zoom magnification based on the position of the first point relative to the second point, the first area, and the candidate area; and
(f) zoom the image in the zoom direction at the zoom magnification to generate a zoomed image having the same aspect ratio as the image, and each side of the image coinciding with that of a second image included in the candidate area, which has a smaller area than the first area, without displaying at least one frame line indicating the candidate area in the zoomed image,
wherein the candidate area is set to have the same aspect ratio as the image and the candidate area is a maximum area inside the first area, and the image is zoomed out into the candidate area, and the candidate area is located at a center of a display range.

2. The information processing apparatus of claim 1, wherein the zoom magnification is determined based on a comparison of a size of the candidate area and a size of the image.

3. The information processing apparatus of claim 1, further comprising:
a storage unit configured to store image data having different resolutions in hierarchical layers;
wherein the instructions further cause the processor to:
determine a zoom magnification based on the position of the first point relative to the second point,
wherein the image is zoomed by reading out image data at a hierarchical layer having a resolution corresponding to the zoom magnification.

4. The information processing apparatus of claim 1, further comprising:
an input device; and
a display,
wherein the instructions further cause the processor to:
display the image on the display;
designate the first point and the second point according to an input received by the input device; and
display the zoomed image according to the input received by the input device.

5. The information processing apparatus of claim 1, wherein the image is of a pathological tissue sample captured by a microscope.

6. An information processing method comprising:
designating a first point and a second point on an image;
determining a zoom direction based on a position of the first point relative to a position of the second point;
setting a first area that is defined based on the first point and the second point, and the first area is a rectangular area having the first point and the second point at two opposite corners;
setting a candidate area in the image based on the zoom direction and the first area, wherein the candidate area is different from the first area, the candidate area includes at least a part the first area, and the candidate area comes into contact with at least one of short sides and long sides of the rectangular area;
determining a zoom magnification based on the position of the first point relative to the second point, the first area, and the candidate area; and
zooming the image in the zoom direction at the zoom magnification to generate a zoomed image having the same aspect ratio as the image, and each side of the image coinciding with that of a second image included in the candidate area, which has a smaller area than the first area, without displaying at least one frame line indicating the candidate area in the zoomed image,
wherein the candidate area is set to have the same aspect ratio as the image and the candidate area is a maximum area inside the first area, and the image is zoomed out into the candidate area, and the candidate area is located at a center of a display range.

7. The information processing method of claim 6, wherein the zoom magnification is determined based on a comparison of a size of the candidate area and a size of the image.

8. The information processing method of claim 6, further comprising:
storing image data having different resolutions in hierarchical layers; and
determining a zoom magnification based on the position of the first point relative to the second point;
wherein the image is zoomed by reading out image data at a hierarchical layer having a resolution corresponding to the zoom magnification.

9. The information processing method of claim 6, further comprising:
displaying the image on a display;
receiving an input from an input device;
designating the first point and the second point according to the input; and
displaying the zoomed image according to the input.

10. The information processing method of claim 6, wherein the image is of a pathological tissue sample captured by a microscope.

11. A non-transitory computer readable storage medium storing a computer program for causing an information processing apparatus to:
designate a first point and a second point on an image;
determine a zoom direction based on a position of the first point relative to a position of the second point;
set a first area that is defined based on the first point and the second point, and the first area is a rectangular area having the first point and the second point at two opposite corners;
set a candidate area in the image based on the zoom direction and the first area, wherein the candidate area is different from the first area, the candidate area includes at least a part the first area, and the candidate area comes into contact with at least one of short sides and long sides of the rectangular area;
determine a zoom magnification based on the position of the first point relative to the second point, the first area, and the candidate area; and
zoom the image in the zoom direction at the zoom magnification to generate a zoomed image having the same aspect ratio as the image, and each side of the image coinciding with that of a second image included in the candidate area, which has a smaller area than the first area, without displaying at least one frame line indicating the candidate area in the zoomed image,
wherein the candidate area is set to have the same aspect ratio as the image and the candidate area is a maximum area inside the first area, and the image is zoomed out into the candidate area, and the candidate area is located at a center of a display range.

12. The non-transitory computer readable storage medium of claim 11, wherein the zoom magnification is determined based on a comparison of a size of the candidate area and a size of the image.

13. The non-transitory computer readable storage medium of claim 11, wherein the information processing apparatus is further caused to:
 store image data having different resolutions in hierarchical layers; and
 determine a zoom magnification based on the position of the first point relative to the second point,
 wherein the image is zoomed by reading out image data at a hierarchical layer having a resolution corresponding to the zoom magnification.

14. The non-transitory computer readable storage medium of claim 11, wherein the information processing apparatus is further caused to:
 display the image on a display;
 receive an input from an input device;
 designate the first point and the second point according to the input; and
 display the zoomed image according to the input.

15. The non-transitory computer readable storage medium of claim 11, wherein the image is of a pathological tissue sample captured by a microscope.

\* \* \* \* \*